US011826382B2

(12) United States Patent
Bundschuh et al.

(10) Patent No.: US 11,826,382 B2
(45) **Date of Patent: *Nov. 28, 2023**

(54) THERAPEUTIC MATERIAL WITH LOW PH AND LOW TOXICITY ACTIVE AGAINST AT LEAST ONE PATHOGEN FOR ADDRESSING PATIENTS WITH RESPIRATORY ILLNESSES

(71) Applicant: Tygrus, LLC, Troy, MI (US)

(72) Inventors: Paul Bundschuh, Austin, TX (US); Lawrence Carlson, North Branch, MI (US); Shawn Dolan, Sterling Heights, MI (US); Andrew M. Yaksic, Brighton, MI (US)

(73) Assignee: Tygrus, LLC, Troy, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,624

(22) Filed: Dec. 10, 2021

(65) Prior Publication Data

US 2022/0096536 A1 Mar. 31, 2022

Related U.S. Application Data

(63) Continuation of application No. PCT/US2021/056001, filed on Oct. 21, 2021, which is a continuation-in-part of application No. PCT/US2021/030429, filed on May 3, 2021, and a continuation-in-part of application No. PCT/US2021/030429, filed on May 3, 2021, and a continuation-in-part of application No. 17/246,887, filed on May 3, 2021.

(60) Provisional application No. 63/220,441, filed on Jul. 9, 2021, provisional application No. 63/158,864, filed on Mar. 9, 2021, provisional application No. 63/144,305, filed on Feb. 1, 2021, provisional application No. 63/121,856, filed on Dec. 4, 2020, provisional application No. 63/019,258, filed on May 1, 2020.

(51) Int. Cl.

| | |
|---|---|
| ***A61K 33/04*** | (2006.01) |
| ***A61K 33/06*** | (2006.01) |
| ***A61K 31/14*** | (2006.01) |
| ***A61K 33/20*** | (2006.01) |
| ***A61P 31/04*** | (2006.01) |
| ***A61K 9/00*** | (2006.01) |
| ***A61P 31/14*** | (2006.01) |

(52) U.S. Cl.

CPC ............ *A61K 33/04* (2013.01); *A61K 9/0073* (2013.01); *A61K 31/14* (2013.01); *A61K 33/06* (2013.01); *A61K 33/20* (2013.01); *A61P 31/04* (2018.01); *A61P 31/14* (2018.01)

(58) Field of Classification Search

CPC .............................. A61P 31/14; A61K 9/0073

See application file for complete search history.

(56) References Cited

U.S. PATENT DOCUMENTS

| | | | | |
|---|---|---|---|---|
| 4,853,416 | A | 8/1989 | Anaebonam et al. | |
| 5,192,528 | A | 3/1993 | Radhakrislman | |
| 5,858,201 | A | 1/1999 | Otsuka et al. | |
| 6,040,344 | A | 3/2000 | Gao et al. | |
| 6,716,414 | B2 | 4/2004 | Lewis et al. | |
| 8,158,677 | B2 * | 4/2012 | Munger | A61K 31/34 514/473 |
| 2005/0080043 | A1 | 4/2005 | Shahinian | |
| 2005/0139808 | A1 | 6/2005 | Alimi | |
| 2005/0226972 | A1 * | 10/2005 | Kemp | C12H 1/10 426/321 |
| 2006/0193785 | A1 | 8/2006 | Lewis et al. | |
| 2007/0196434 | A1 | 8/2007 | Alimi et al. | |
| 2007/0274926 | A1 | 11/2007 | Fuls et al. | |
| 2010/0285151 | A1 | 11/2010 | Goldan et al. | |
| 2011/0135713 | A1 | 6/2011 | Dale | |
| 2012/0269904 | A1 | 10/2012 | Northey | |
| 2014/0322285 | A1 * | 10/2014 | Bui | A01N 59/00 |
| 2019/0029254 | A1 | 1/2019 | Rehdorf et al. | |
| 2019/0046488 | A1 | 2/2019 | Rosenblatt et al. | |
| 2019/0216831 | A1 * | 7/2019 | Carvalho | A61K 31/675 |
| 2020/0281969 | A1 | 9/2020 | Burd | |
| 2021/0060050 | A1 | 3/2021 | Painter et al. | |
| 2022/0096536 | A1 | 3/2022 | Bundschuh et al. | |
| 2022/0133786 | A1 | 5/2022 | Bundschuh et al. | |

FOREIGN PATENT DOCUMENTS

| | | | | |
|---|---|---|---|---|
| DE | 10118776 | A1 | 11/2002 | |
| JP | 6165953 | B1 * | 7/2017 | A01N 25/02 |
| WO | 0048477 | A2 | 8/2000 | |

(Continued)

OTHER PUBLICATIONS

JP6165953B1, Escapenet Machine Translation, downloaded in Apr. 2022 (Year: 2022).*

Timothy R Myers, The Science Guiding Selection of an Aerosol Delivery Device, Respiratory Care, vol. 58, No. 11, Nov. 2013 (Year: 2013).*

Reagents, Formic Acid, 2% (v/v) Standardized, publication date: Nov. 29, 2017 (Year: 2017).*

International Search Report and Written Opinion in PCT/US2021/056001, dated Jan. 14, 2022 (17 pages).

(Continued)

*Primary Examiner* — Mark V Stevens

*Assistant Examiner* — Alparslan Asan

(74) *Attorney, Agent, or Firm* — Young Basile Hanlon & MacFarlane, P.C.

(57) ABSTRACT

Method and composition for treating or preventing a respiratory illness. The method includes administering at least one dose of a pharmaceutically acceptable fluid having a pH less than 3.0 into contact with at least one region of the respiratory tract present in a patient in need thereof. Respiratory illness that can be treated include COVID-19.

15 Claims, No Drawings

(56) References Cited

FOREIGN PATENT DOCUMENTS

| | | | | |
|---|---|---|---|---|
| WO | 2001028340 | A2 | | 4/2001 |
| WO | 02/38154 | A1 | | 5/2002 |
| WO | 2014037726 | A1 | | 3/2014 |
| WO | 2017/173340 | A1 | | 10/2017 |
| WO | 2018/017735 | A1 | | 1/2018 |
| WO | WO2019142214 | A1 | * | 7/2019 |
| WO | 2021/001789 | A1 | | 1/2021 |

OTHER PUBLICATIONS

International Search Report and the Written Opinion of the International Searching Authority, or the Declaration for International Patent Application No. PCT/US2021/030429, dated Aug. 20, 2021, 15 pages.

Pianta, L et al., "Acetic acid disinfection as a potential adjunctive therapy," Eur. Arch. Ororhinolaryngol, vol. 277, Issue 10, pp. 2921-2924.

Edwards et al., "A New Natural Defense Against Airborne Pathogens," QRB Discovery, vol. 1, Article E5.

Darnell, M. et al., "Inactivation of the coronavirus that induces severe acute respiratory syndrome, SARS-CoV," J. Virologicai Methods, vol. 121, pp. 85-91.

Ernstagard, L. et al. "Acute effects of exposure to vapours of acetic acid in humans," Toxicology Letters, vol. 165, pp. 22-30.

De Benedictis, P. et al., "Inactivation of Avian Influenza Viruses by Chemical Agents and Physical Conditions: A Review," Zoonoses and Public Health, vol. 2, pp. 51-68.

Yoshimoto, J. et al., "Virucidal effect of acetic acid and vinegar on SARS-CoV-2," Research Square Preprint, DOI 10.21203/rs.3.rs-37750/v1.

Koenig, J. et al., "The Effect of Duration of Exposure on Sulfuric Acid-induced Pulmonary Function Changes in Asthmatic Adolescent Subjects: A Dose-response Study," Toxicology and Industrial Health, vol. 8, No. 5, pp. 285-296.

Dahl, A. et al., "Clearance of Sulfuric Acid-Introduced 35S from the Respiratory Tracts of Rats, Guinea Pigs and Dogs Following Inhalation or Instillation," Fundamental and Applied Toxicology, vol. 3, pp. 293-297.

OECD SIDS (2001), "Sulfuric Acid," UNEP Publications. 44 pages.

Forum of International Respiratory Societies. "The Global Impact of Respiratory Disease—Second Edition. Sheffield, European Respiratory Society." (2017).

Caruso, A. et al., "Might hydrogen peroxide reduce the hospitalization rate and complications of SARS-CoV-2 Infection?" Infection Control & Hospital Epidemiology, vol. 41, Issue 11, pp. 1360-1361.

Trejo, A. C. et al., "Hydrogen Peroxide as an Adjuvant Therapy for COVID-19: A Case Series of Patients and Caregivers in the Mexico City Metropolitan Area," Evidence-Based Complementary and Alternative Medicine, vol. 2021, article ID 5592042, 12 pages.

Borghardt, J. M. et al., "Inhaled Therapy in Respiratory Disease: The Complex Interplay of Pulmonary Kinetic Processes," Canadian Respiratory Journal, vol. 2018, Article ID 2732017, 11 pages.

Edwards, D. et al., "Nasal Calcium-Rich Salts for Cleaning Airborne Particles from the Airways of Essential Workers, Students, and a Family in Quarantine," Molecular Frontiers Journal, vol. 4, Nos. 1 & 2, pp. 36-45.

Abou Alaiwa, M. et al., "Repurposing tromethamine as inhaled therapy to treat CF airway disease," JCI Insight, vol. 1, No. 8, 12 pages.

Grasemann, H. et al., "A randomized controlled trial of inhaled L-Arginine in patients with cystic fibrosis," Journal of Cystic Fibrosis, vol. 12, pp. 468-474.

Pagani, I. et al., "Vinegar and its active component acetic acid inhibit SARS-CoV-2 Infection in vitro and ex vivo," Journal of Translational Science, vol. 7, Issue 3.

Chan, K-H. et al., "Factors affecting stability and infectivity of SARS-CoV-2," Journal of Hospital Infection, vol. 106, Issue 2, pp. 226-231.

Stein et al., The History of Therapeutic Aerosols: A Chronological Review, Journal of Aerosol Medicine and Pulmonary Drug Delivery, vol. 30, No. 1, 2017. (pp. 20-41).

Notification of Transmittal of the International Search Report and the Written Opinion of the International Searching Authority, or the Declaration for International Patent Application No. PCT/US2021/030429, dated Aug. 20, 2021, 15 pages.

Ryan et al., Safety of a Preservative-Free Acidified Saline Nasal Spray, A Randomized, Dou.Me-blind, PlacetJO-Controlled, Crossover Clinical Trial. (5 pages).

Gupta et al., Salts of Therapeutic Agents: Chemical, Physicochemical, and Biological Considerations, Molecules. (15 pages).

Gern et al., Inhibition of Rhinovirus Replication In Vitro and In Vivo by Acid-Buffered Saline. (7 pages).

Pilaniya et al., Recent trends in the impurity profile of pharmaceuticals. (9 pages).

Higgins et al., Intranasal Antiviral Drug Delivery and Coronavirus Disease 2019 (COVID-19):A State of the Art Review. (13 pages).

International Preliminary Report on Patentability for International Patent Application No. PCT/US2021/030429, dated Nov. 10, 2022, 9 pages.

Written Opinion of the International Preliminary Examining Authority for International Patent Application No. PCT/US2021/056001, dated Nov. 7, 2022, 250 pages.

* cited by examiner

THERAPEUTIC MATERIAL WITH LOW PH AND LOW TOXICITY ACTIVE AGAINST AT LEAST ONE PATHOGEN FOR ADDRESSING PATIENTS WITH RESPIRATORY ILLNESSES

CROSS-REFERENCE TO PENDING APPLICATIONS

The present application is a continuation of PCT/US2021/056001 filed Oct. 21, 2021, the specification of which is incorporated by reference herein, which is a continuation in part of PCT/US2021/030429 filed May 3, 2021, and claims priority to U.S. Provisional Application Ser. No. 63/121,856 filed Dec. 4, 2020; to U.S. Provisional Application Ser. No. 63/144,305 filed Feb. 1, 2021; to U.S. Provisional Application Ser. No. 63/158,864 filed Mar. 9, 2021 and to U.S. Provisional Application Ser. No. 63/220,441 filed Jul. 9, 2021. The present application also claims priority to U.S. Provisional Application Ser. No. 63/144,305 filed Feb. 1, 2021; to U.S. Provisional Application Ser. No. 63/158,864 filed Mar. 9, 2021 and to U.S. Provisional Application Ser. No. 63/220,441 filed Jul. 9, 2021, the specifications of which are incorporated in their entirety herein. The present application is a continuation in part of PCT/US2021/030429 filed May 3, 2021, the specification of which is incorporated by reference herein, which claims priority to U.S. Provisional Application Ser. No. 63/144,305 filed Feb. 1, 2021; to U.S. Provisional Application Ser. No. 63/121,856 filed Dec. 4, 2020; and to U.S. Provisional Application No. 63/019,258 filed May 1, 2020. The present application is a continuation in part of U.S. Application Ser. No. 17,246,887 filed May 5, 2021, which claims priority to U.S. Provisional Application Ser. No. 63/144,305 filed Feb. 1, 2021 and to U.S. Provisional Application Ser. No. 63/121,856 filed Dec. 4, 2020.

BACKGROUND

The present disclosure is directed to a method and composition for treating and/or preventing a respiratory illness. More particularly, the present disclosure is directed to a method for treating and/or preventing a respiratory illness caused, at least in part by an infectious pathogen. Non limiting examples of such pathogens are bacterial pathogens, fungal pathogens and/or viral pathogens. A non-limiting example of viral pathogens include those caused by one of more of coronaviruses, influenzas viruses, parainfluenza viruses, respiratory syncytial viruses, and rhinoviruses.

Infectious respiratory diseases challenge the health, safety, and well-being of people of all ages. Various viral and/or bacterial and/or fungal pathogens can spread readily through populations infecting many. This is particularly challenging when large numbers of individuals in the affected population lacks natural or acquired immunities to the given pathogen. It is also challenging in populations with limited or no access to advanced medical treatment. Therefore, rural regions in the developed countries such as the United States as well as many regions in countries in Africa, South America and Asia can find the arrival of novel infectious pathogens, particularly difficult if not devastating.

Respiratory pathogens such as bacteria, fungi, and viruses including SARS-CoV-2, kill over five million people annually. (Forum of International Respiratory Societies. The Global Impact of Respiratory Disease—Second Edition. Sheffield, European Respiratory Society, 2017)._In the case of emerging pandemic pathogens such as SARS-CoV-2, disease specific therapeutics take time to develop. Also, many endemic pathogens can evolve to become multi-drug resistant, can exhibit multiple genotypes, and can present rapidly without specific diagnostic platforms available until exponential disease transmission has occurred. Available therapeutics are often pathogen specific. The timeline for therapeutic development from pathogen characterization, target identification, small molecule design, to clinical testing is costly and may take years to achieve. For example, the SARS-CoV-2 virus has mutated into multiple variants to increase its transmission and productive infection rates and will likely further mutate to circumvent antibody recognition generated within vaccinated populations.

A broad-spectrum antimicrobial therapy that offers efficacy across many viral, bacterial, and fungal respiratory pathogens is highly desirable. It is also desirable to provide efficacy against current and emerging SARS-CoV-2 variants as well as current and emerging antibiotic-resistant bacteria strains. Additionally, it is desirable that the therapeutic is easy to administer, demonstrates minimal systemic effects and is broadly available for all patient access, which may enable use as a first-line treatment option for a wide range of respiratory infections prior to or in addition to pathogen-specific drug materials and/or treatment methods.

Medical investigations for inhaled pulmonary antimicrobial compounds effective against infectious pathogens that can proliferate in one or more regions of the respiratory tract began over a century ago as a potential therapeutic for infections diseases such as tuberculosis and wells as common colds influenza and the like. The search was not successful, and this effort appears to have been eclipsed by the discovery of antibiotics such as penicillin. However, the need for a safe and effective pulmonary antimicrobial compounds and compositions continues has become more urgent due to the COVID-19 pandemic. Additionally, the proliferation of antibiotic and therapeutic resistant pathogens as well as a growing patient population with pre-existing respiratory diseases that can increase their susceptibility to a wide range of viral, bacterial, and fungal respiratory pathogens also underscores the need for effective pulmonary antimicrobial compounds and treatments.

Additionally, upper and lower respiratory tract infections are commonly treated with antibiotics and can be the reason for over half of the antibiotic prescriptions in developed industrialized countries. This can be costly and may increase the emergence of antibiotic resistant strains of pathogens over time. Thus, it would be desirable to provide a composition and treatment that could be employed as a treatment in respiratory tract infections as either and alternative or, at minimum, an adjunct to antibiotic treatment.

The need for a pulmonary antiseptic compound that is pharmaceutically acceptable, effective, within patient administration tolerance levels and non-deleterious to host tissue has yet to be met.

Thus, it would be desirable to provide a formulation or formulations that can act against one or more pathogens in situ in a patient in order to reduce or eliminate one or more pathogens associated with respiratory infection. It is also desirable to provide a method for preventing an infection or treating a patient presenting with an infection caused by one or more pathogens or testing positive for pathogens that is pharmaceutically acceptable, effective, tolerable and non-deleterious to host tissue.

SUMMARY

Disclosed is a method of treating or preventing a respiratory illness that includes administering at least one dose of a pharmaceutically acceptable fluid having a pH less than 3.0 into contact with at least one region of the respiratory tract of the patient in need thereof. The pharmaceutically acceptable fluid can include at least one inorganic acid, at least one organic acid and mixtures thereof.

Also disclosed is a therapeutic composition that includes a fluid carrier and an acidic component that includes a pharmaceutically acceptable acidic component present in an amount sufficient to produce a pH less than 3.0 for use in addressing a respiratory illness in a patient in need thereof. The pharmaceutically acceptable acidic component can be at least one inorganic acid, at least one organic acid and mixtures thereof.

Also disclosed is a composition having a pH below 3.0 composed of at least one pharmaceutically acceptable acid used as a therapeutic inhalant composition. The at least one pharmaceutically acceptable acid can be at least one inorganic acid, at least one organic acid or mixtures thereof.

Also disclosed is a kit for use in the treatment or prevention of a respiratory illness comprising a pharmaceutically acceptable fluid which comprises a liquid carrier and at least one compound wherein the pharmaceutically acceptable fluid has a pH less than 3.0 and a container for administering the pharmaceutically acceptable fluid into the respiratory tract of a patient in need thereof.

DETAILED DESCRIPTION

Disclosed herein is a method of and composition for treating or preventing a respiratory illness that includes the step of administering at least one dose of a pharmaceutically acceptable fluid having a pH less than 3.0 into contact with at least one region of the respiratory tract present in the patient in need thereof.

Respiratory illnesses that can be treated or prevented by the method and/or composition as disclosed herein can include respiratory tract infections caused be one or more a variety of infectious pathogens which can affect humans or animals or both. Respiratory illness that can be treated or prevented by the method as disclosed herein can include one or more chronic respiratory conditions. Respiratory illnesses that can be treated or prevented can be a combination of one or more chronic respiratory conditions and one or more respiratory infections. In certain embodiments respiratory tract infections can be either acute infections or chronic infections and can be caused by one or more pathogens. It is also contemplated that respiratory illnesses can be a combination of the chronic respiratory illness(es) and respiratory tract infection(s).

Chronic respiratory conditions as defined by the United States Center for Disease Control are defined broadly as conditions that last one year or more and require ongoing medical attention or curtail activities of daily living or both. Non-limiting examples of chronic respiratory illnesses that can be addressed by the method and/or composition disclose herein include chronic obstructive pulmonary disease, cystic fibrosis, asthma, or respiratory allergies.

Respiratory tract infections as that term in used in this disclosure is broadly defined as any infectious disease of the upper or lower respiratory tract. Upper respiratory tract infections can include, but are not limited to, the common cold, laryngitis, pharyngitis/tonsillitis, rhinitis, rhinosinusitis, and the like. Lower respiratory tract infections include bronchitis, bronchiolitis, pneumonia, tracheitis and the like.

Pathogens responsible for respiratory tract infections that can be treated by the method and/or composition as disclosed herein can include one or more viral pathogens, one or more bacterial pathogens, one or more fungal pathogens as well as mixed pathogen infections arising from two or more of the classes discussed. In certain embodiments disclosed herein, the viral pathogen can be at least one of a coronavirus, an influenza virus, a parainfluenza virus, a respiratory syncytial virus (RSV), a rhinovirus, an adenovirus as well as combinations of two or more of the foregoing. It is also contemplated that the various viral strains causing infection in a patient can be pure strains or can be mixtures of various strains, types, subtypes and/or mutations.

Coronaviruses that can be treated by the method and/or composition as disclosed herein include, but are not limited to, alpha coronaviruses, beta coronavirus as well as other emergent types. Coronaviruses, as that term is employed in this disclosure, are understood to be a group of related RNA viruses that cause disease, particularly respiratory tract infections in various mammalian and avian species. Coronaviruses that can be treated by the method and/or composition as disclosed herein include members of the subfamily Orthocoronavirinae in the family Coronaviridea. In certain embodiments, the method and/or composition as disclosed herein can be employed to treat or prevent respiratory infections in which the diseases-causing pathogen is a human coronavirus that is member of the family Coronaviridea selected from the group consisting of SARS-CoV-1 (2003), HCoV NL63(2004), HCoV HKU1 (2004), MERS-CoV (2013) SARS-CoV-2 (2019) and mixtures thereof. In certain embodiments the coronavirus can be a beta coronavirus selected from the group consisting of SARS-CoV, SARS-CoV-2, MERS-CoV, and mixtures thereof. In certain embodiments the method and/or composition as disclosed herein can be employed to treat or prevent respiratory infections in which the diseases-causing pathogen is an enveloped, positive-sense, single stranded RNA virus other than those mentioned.

Non-limiting examples of influenza viruses that can cause respiratory tract infections and can be treated by the method and/or compositions as disclosed herein can be negative-sense RNA viruses such as Orthomyxoviridae such as those from the genera: alphainfluenza, betainfluenza, deltainfluenza, gammainfluenza, thogotovirus and quarajavirus. In certain embodiments, the influenza virus can be an alphainfluenza that expresses as a serotype such as H1N1, H1N2, H2N2, H3N1, H3N2, H3N8, H5N1, H5N2, H5N3, H5N8, H5N9, H7N1, H7N2, H7N4, N7N7, H7N9, H9N2, H10N7. Other expressions are also contemplated.

Non-limiting examples of parainfluenza viruses can be single-stranded, enveloped RNA viruses of the Paramyoviridae family. Non-limiting examples of human parainfluenza viruses include those in the genus Respirovirus and those in the genus Rubulavirus.

Non-limiting examples of respiratory syncytial viruses (RSV) are various medium sized (~150 nm) enveloped viruses from the family Pneumvidae such as those in the genus Orthopneumovirus.

Non-limiting examples of rhinovirus that can be treated by the method and/or composition as disclosed herein include those with single-stranded positive sense RNA genomes that are composed of a capsid containing the viral protein(s). Rhinoviruses can be from the family Picovirus and the genus Enterovirus.

Non-limiting examples of adenoviruses include non-enveloped viruses such as those with an icosahedral nucleocapsid containing nucleic acid such as double stranded DNA. Viruses can be from the family Adenoviridae and genera such as Atadenovirus, Mastadenvirus, Siadenovirus, and the like.

It is also contemplated that the method and/or composition as disclosed herein can be used to treat respiratory infections caused by bacterial pathogens. Non-limiting examples of such bacterial pathogens include *Streptococcus pneumoniae, Pseudomonas aeruginosa, Klebsiella pneumoniae, Haemophilus influenzae, Staphylococcus aureus, Moraxella catarrhalis, Streptococcus pyogenes, Mycobacterium tuberculosis, Mycobacterium avium—intracellulare* (MAI), *Mycobacterium terrae*, and mixtures thereof.

The method and/or composition as disclosed herein can be used to treat respiratory infections caused by fungal pathogens presenting as single-pathogen fungal infections, multi-pathogen fungal infections or general mycosis with respiratory involvement. Non-limiting examples of fungal pathogens implicated in respiratory illnesses and infections include certain species from the genus *Aspergillus*, with *A. fumigatus, A. flavus*, and *A. clavatus* being non-limiting examples. Other examples of respiratory infections caused by fungal pathogens that can be treated by the method and/or compositions disclosed herein are respiratory infections involving infectious species of *Cryptococcus, Rhizopus, Mucor, Pneumocystis, Candida*, and the like.

In certain embodiments, the method and/or composition as disclosed herein can have a pH less than 2.8; less than 2.5; less than 2.4; less than 2.0; less than 1.8; less than 1.7; less than 1.6; less than 1.5; less than 1.0 with lower ranges being determined by the lung condition and health of the patient. In certain embodiments, the composition can have a have a pH between 1.4 and 3.0 between 1.5 and 3.0; between 1.6 and 3.0; between 1.7 and 3.0; between 1.8 and 3.0; between 1.9 and 3.0; between 2.0 and 3.0; between 2.2 and 3.0; between 2.4 and 3.0; between 1.4 and 2.5; between 1.5 and 2.5; between 1.6 and 2.5; between 1.7 and 2.5; between 1.8 and 2.5; between 1.9 and 2.5; between 2.0 and 2.5; between 2.2 and 2.5; between 2.4 and 2.5; between 1.4 and 2.4; between 1.5 and 2.4; between 1.6 and 2.4; between 1.7 and 2.4; between 1.8 and 2.4; between 1.9 and 2.4; between 2.0 and 2.4; between 2.2 and 2.4; between 1.4 and 2.4; between 1.5 and 2.2; between 1.6 and 2.2; between 1.7 and 2.2; between 1.8 and 2.2; between 1.9 and 2.2; between 2.0 and 2.2; between 1.4 and 2.0; between 1.5 and 2.0; between 1.6 and 2.0; between 1.7 and 2.0; between 1.8 and 2.0; between 1.9 and 2.0, between 1.4 and 1.9; between 1.4 and 1.9; between 1.4 and 1.8; between 1.4 and 1.7; between 1.4 and 1.6; between 1.4 and 1.5.

In the method as disclosed herein, the pharmaceutically acceptable fluid having a pH below 3.0 can be administered into contact with at least one region of the respiratory tract of the patient in need thereof can be administered by any therapeutically acceptable manner. In certain embodiments, the pharmaceutically acceptable fluid will be administered in a manner that permits or promotes uptake of at least a portion of the composition by patient inhalation. The pharmaceutically acceptable fluid can be introduced under pressure in certain embodiments.

The pharmaceutically acceptable fluid as disclosed herein can be introduced into contact with at least one region in the respiratory tract of the patient in the form of a gas, a fluid or a mixture of the two. In certain embodiments, the pharmaceutically acceptable fluid can also include one or more powders or micronized solids. The pharmaceutically acceptable fluid can be introduced into contact with at least a portion of the respiratory tract of the patient in the form a vapor, aerosol, spray, micronized mist, gas or the like. It is also contemplated that the pharmaceutically acceptable fluid can be administered as a gas, as dispersed nanoparticles in a gas, as micronized particles in a gas, as nanoparticles dispersed in a gas or the like.

The size particulate or droplet material composed of the pharmaceutically acceptable fluid that is introduced into contact with at least one region of the respiratory tract of the patient can be adjusted or tuned to increase contact with the desired region of the respiratory tract. The respective regions of the respiratory tract which the pharmaceutically acceptable fluid can contact can include nose, sinuses, throat, pharynx, larynx, epiglottis, sinuses, trachea, bronchi, alveoli, or combinations of any of the foregoing. The size distribution of the particles/droplets can be tuned to address the location of greatest pathogen population. In certain embodiments, the at least one dose of a pharmaceutically acceptable fluid can be delivered into contact with the lower respiratory tract such as the bronchi, alveoli and the like in order to address infections localized in that region. In certain embodiments, the at least one dose of a pharmaceutically acceptable fluid can be delivered into contact with the upper respiratory tract such as the nose or nostrils, nasal cavity, mouth, pharynx, larynx and the like to address infections localized in this region.

In certain embodiments, the pharmaceutically acceptable fluid as administered can have a particle size between 0.1 and 20.0 microns mean mass aerodynamic diameter (MMAD). In certain embodiments, the particle size can be between 0.5 and 20.0; between 0.75 and 20.0; between 1.0 and 20.0; between 2.0 and 20.0; between 3.0 and 20.0; between 4.0 and 20.0; between 5.0 and 20.0; between 7.0 and 20.0; between 10.0 and 20.0; between 12.0 and 20.0; between 15.0 and 20.0; between 16.0 and 20.0; between 17.0 and 20.0; between 18.0 and 20.0; between 0.1 and 15.0; between 0.5 and 15.0; between 0.75 and 15.0; between 1.0 and 15.0; between 2.0 and 15.0; between 3.0 and 15.0; between 4.0 and 15.0; between 5.0 and 15.0; between 7.0 and 15.0; between 10.0 and 15.0; between 12.0 and 15.0; between 14.0 and 15.0; between 0.1 and 10.0; between 0.5 and 10.0; between 0.75 and 10.0; between 1.0 and 10.0; between 2.0 and 10.0; between 3.0 and 10.0; between 4.0 and 10.0; between 5.0 and 10.0; between 7.0 and 10.0; between 8.0 and 10.0; between 9.0 and 10.0; between 0.1 and 5.0; between 0.5 and 5.0; between 0.75 and 5.0; between 1.0 and 5.0; between 2.0 and 5.0; between 3.0 and 5.0; between 4.0 and 5.0; between 0.1 and 4.0; between 0.5 and 4.0; between 0.75 and 4.0; between 1.0 and 4.0; between 2.0 and 4.0; between 3.0 and 4.0; between 0.1 and 3.0; between 0.5 and 3.0; between 0.75 and 3.0; between 1.0 and 3.0; between 1.5 and 3.0; between 2.0 and 3.0; between 0.1 and 2.0; between 0.5 and 2.0; between 0.75 and 2.0; between 1.0 and 2.0; between 1.5 and 2.0; between 0.1 and 1.0; between 0.3 and 1.0; between 0.5 and 1.0; between 0.75 and 1.0 microns.

The pharmaceutically acceptable fluid can be introduced into contact with at least one region of the respiratory tract of the patient at a concentration and in an amount sufficient to reduce pathogen load present in the respiratory tract. It is within the purview of this disclosure that the pharmaceutically acceptable fluid can be introduced continually over a defined interval of minutes, hours or even days. In certain embodiments, the pharmaceutically acceptable fluid can be introduced continuously for an interval of at least 24 hours. In patients presenting with respiratory infections, continuous administration can be discontinued upon reduction in pathogen load either as directly measured or indirectly ascertained by improvement in symptoms such as blood oxygen saturation or the like.

It is also within the purview of this disclosure that the pharmaceutically acceptable fluid can be administered in a series of at least two doses introduced at defined intervals. The intervals for dosing and number of doses administered will be that sufficient to reduce the pathogen load present in the respiratory tract of the patient either as directly measured or indirectly ascertained by improvement in symptoms such as blood oxygen saturation or the like.

In certain embodiments, the reduction in pathogen load can be a partial or complete reduction in the pathogen count in the respiratory tract of the patient to whom the pharmaceutically acceptable fluid is administered. Where less than complete reduction in respiratory tract pathogen count is achieved, it is believed that respiratory tract pathogen count reduction, in at least some instances can be sufficient to permit the patient's own immune system response to address or overcome the infectious pathogen either alone or with additional supportive or augmented therapy.

Where the pharmaceutically acceptable fluid is administered in a plurality of discrete doses, it is contemplated that the pharmaceutically acceptable fluid can be administered over 2 to 10 doses in a 24-hour period, with 3 to 4 doses being contemplated in certain embodiments. Each dosing interval can be for a period of 1 second to 120 minutes, with administration intervals between 1 and 60 minutes; 1 and 30 minutes; 1 and 20 minutes; 1 and 10 minutes being contemplated in certain embodiments. In certain embodiments, where the pharmaceutically acceptable fluid is administered over a dosing interval, an additional portion of the pharmaceutically acceptable fluid is introduced over the dosing interval and is brought into contact with the affected portion respiratory tract thereby reducing pathogen load with the continuing addition.

Direct measurement of the reduction in pathogen load in the respiratory tract of the patient can be accomplished by any suitable mechanism such as by swabbing, sampling or the like. In certain embodiments it is contemplated that the reduction in pathogen load can be defined as at least 1% reduction of pathogen population in at least one region of the respiratory tract of the patient as measured at a time between 1 minute and 24 hours after commencement of administration. In certain embodiments, the reduction in pathogen load can be at least 10% as measured at a time between 1 minute and 24 hours after commencement of administration; at least 25%; at least 50%; at least 75%.

It is contemplated that the pharmaceutically acceptable fluid can be administered prophylactically or therapeutically depending on the physiology and health history of the specific patient. A non-limiting example of prophylactic administration can include routine administration of the pharmaceutically acceptable fluid in a suitable dosing regimen to individuals presenting with a chronic condition with increased risk for respiratory tract infection or complications due to a respiratory tract infection. Another non-limiting example of prophylactic administration is administration of one or more doses of the pharmaceutically acceptable fluid as disclosed herein after exposure to a contagious pathogen.

It is contemplated that administration of the pharmaceutically acceptable fluid can be accomplished by one or more suitable devices including, but not limited to, nebulizers, cool mist vaporizers, positive pressure inhalers, CPAP units and the like.

The pharmaceutically acceptable fluid can include at least one acid compound that is present at a concentration sufficient to provide a fluid pH less than 3.0 and within the ranges recited in this disclosure. The pharmaceutically acceptable fluid can include at least one acid present in a suitable carrier as desired or required. The acid that is employed can be one which is pharmaceutically acceptable, effective, tolerable and non-deleterious to the surrounding tissue present in the respiratory tract of the patient being treated. Suitable acid compounds can be selected from the group consisting of Brönsted acids, Lewis acids and mixtures thereof.

As used herein the term "pharmaceutically acceptable" is defined as having suitable pharmacodynamics and pharmacokinetics such that the therapeutic material is active primarily on the surface of the tissue of the respiratory tract with little or no systemic effect. Ideally, the materials employed produce residual products that are recognized by the body as common metabolites that are rapidly absorbed and metabolized. "Effective" as used herein is defined as materials that are to be effective on the targeted pathogen in vivo with the goal of significantly reducing the pathogen load in order to assist and augment the body's natural defenses. "Tolerable" as defined herein is that the material can be tolerated by the patient at the effective therapeutic concentration without undesirable reactions including, but not limited to, irritation, choking, coughing or the like. "Non-deleterious" as used herein is defined as the material being effective at killing the targeted pathogen with little or no negative effect on the tissue of the respiratory tract of the that is in direct contact with the material present at therapeutic concentration levels.

The acid compound employed can be at least one inorganic acid, at least one organic acid or a mixture of at least one inorganic acid and at least one organic acid.

In certain embodiments, pharmaceutically acceptable fluid will include and can be at least one inorganic acid present in a concentration sufficient to provide a pH at the levels defined herein. Where two or more inorganic acids are employed, the various inorganic acids will present at a ratio sufficient to provide a pH level within the parameters defined in this disclosure. The ratio of respective acids can be modified or altered to meet parameters such as tolerability. Non-limiting examples of suitable inorganic acids include an inorganic acid selected from the group consisting of hydrochloric acid, phosphoric acid, sulfuric acid, hydrobromic acid, phosphoric acid, polyphosphoric acid, hypochlorous acid, and mixtures thereof. In certain embodiments, the pharmaceutically acceptable fluid can include sulfuric acid, hydrochloric acid, hydrobromic acid and mixtures thereof. The present disclosure also contemplates that the at least one inorganic acid in the pharmaceutically acceptable fluid can be present in whole or in part as a salt or salts of the respective inorganic acid. The at least one inorganic acid can be used alone or in combination with other weak or strong organic or inorganic acids or salts thereof in order to obtain the desired pH range.

In certain embodiments, the pharmaceutically acceptable fluid can include at least one organic acid present in a concentration sufficient to provide a pH at the levels defined herein. In certain embodiments, the at least one organic acid can be present alone or in combination with one or more inorganic acids. Where two or more organic acids are employed, the various organic acids can be present at a ratio sufficient to provide a pH level within the parameters defined in this disclosure. The ratio of respective acids can be modified or altered to meet parameters such as tolerability. Non-limiting examples of organic acids include at least one organic acid selected from the group consisting of acetic acid, trichloroacetic acid, benzenesulfonic acid, citric acid, propionic acid, formic acid, gluconic acid, lactic acid, ascorbic acid, isoascorbic acid, aspartic acid, glutamic acid, glutaric acid and mixtures thereof. In certain embodiments, the organic acid can be at least one of trichloroacetic acid, benzenesulfonic acid, citric acid, propionic acid, formic acid, gluconic acid, lactic acid, ascorbic acid, isoascorbic acid, aspartic acid, glutamic acid, and mixtures thereof.

In certain embodiments, the pharmaceutically acceptable fluid can include at least one inorganic acid in combination with at least one organic acid listed above. It is also contemplated that the at least one organic acid or the at least one inorganic acid can be present in combination with at least one amino acid. Non-limiting examples of such combination includes for example an amino acid such as aspartic acid or glutamic acid and at least one inorganic acid such as hydrochloric acid, hydrobromic acid, and sulfuric acid required to provide the proper pH range.

It is within the purview of this disclosure to provide an acid component present in the pharmaceutically acceptable fluid that can include two or more acid compounds in sufficient concentrations to provide the pharmaceutically acceptable fluid with a pH below 3 or in one of the ranges discussed herein. Thus, it is contemplated that, where two or more acid compounds are present in the pharmaceutically acceptable fluid, the composition can include certain organic and/or inorganic acids that have a pH outside the range levels outlined for the finished composition. It also considered within the purview of this disclosure to include minor amounts of acid compounds at levels which permit them to be tolerated and/or effectively metabolized as needed.

Where desired or required, the pharmaceutically acceptable therapeutic fluid can include a fluid carrier. The fluid carrier component can be a liquid gaseous material suitable for administration to a human, more particularly, the fluid carrier can be one that can be administered as an inhalable or introducible material and come into contact with one or more surfaces present in the at least one region of the respiratory tract of a patient. The fluid carrier component can be a suitable protic solvent, a suitable aprotic solvent or mixtures thereof. In certain embodiments, the carrier can be a fluid that can be gaseous or can be that can be vaporized, aerosolized or the like by suitable means. Non-limiting examples of suitable carriers include water, organic solvents and the like, present alone or in suitable admixture. Non-limiting examples of organic solvents include materials selected from the group consisting of $C_2$ to $C_6$ alcohols, pharmaceutically acceptable fluorine compounds, pharmaceutically acceptable siloxane compounds, pharmaceutically acceptable hydrocarbons, pharmaceutically acceptable halogenated hydrocarbons and mixtures thereof.

Without being bound to any theory, it is believed that free hydrogen present in the pharmaceutically acceptable fluid composition can include one or more suitable acids present in whole or on part in a dissociated state. In certain embodiments, the suitable acid present in a whole or partially dissociated state can be selected from the group consisting of sulfuric acid, hydrochloric acid, hydrobromic acid, carbonic acid, oxalic acid, pyrophosphoric acid, phosphoric acid, and mixtures thereof.

The acid component can be present in an amount sufficient to act on the pathogen present in the respiratory tract of the patient. In certain embodiments, the acid component can be present in an amount up to 10,000 ppm; between 1000 and 10,000 ppm; between 2000 and 10,000 ppm; between 3000 and 10,000 ppm; between 4000 and 10,000 ppm; between 5000 and 10,000 ppm; between 6000 and 10,000 ppm; between 7000 and 10,000 ppm between 8000 and 10,000 ppm; between 9000 and 10,000 ppm. In certain embodiments, the acid component can be present in the pharmaceutically acceptable material solution in an amount between 100 ppm and 2000 ppm; in certain embodiments, the inorganic acid can be present in an amount between 100 ppm and 1700 ppm; between 100 and 1500 ppm; between 100 and 1200 ppm; between 100 and 1000 ppm; between 100 and 900 ppm; between 100 ppm and 800 ppm; between 100 ppm and 700 ppm; and between 100 ppm and 600 ppm. between 500 ppm and 1700 ppm; between 500 and 1500 ppm; between 500 and 1200 ppm; between 500 and 1000 ppm; between 500 and 900 ppm; between 500 ppm and 800 ppm; between 500 ppm and 700 ppm; and between 500 ppm and 600 ppm; between 1000 ppm and 1700 ppm; between 1000 and 1500 ppm; between 1000 and 1200 ppm.

Without being bound to any theory, it is believed acid compound(s) in the pharmaceutically acceptable fluid can function as proton donors which can affect the pathogen(s) present in the at least one region of the respiratory tract of the patient and reduce the pathogen load therein. For example, when sulfuric acid is employed, it at least a portion dissociates at low concentration primarily into hydrogen ions and hydrogen sulfate ($HSO_4^-$) In its dissociated state sulfuric acid can donate protons to affect pathogens. While this mode of action is mentioned, other modes of action are not precluded by this discussion.

The aforementioned compounds can be present in a suitable liquid material. Non-limiting examples of suitable materials include water of a sufficient purity level to facilitate the availability of the component materials and suitability for end-use applications. In certain embodiments, the water component of the liquid material can be material that is classified as ASTM D1193-06 primary grade. Where desired or required, the water component, the water can be purified by any suitable method, including, but not limited to, distillation, double distillation, deionization, demineralization, reverse osmosis, carbon filtration, ultrafiltration, ultraviolet oxidization, microporous filtration, electrodialysis and the like. In certain embodiments, water having a conductivity between 0.05 and 2.00 micro siemens can be employed. It is also within the purview of this disclosure that the water component of the liquid material can be composed of water having a purity greater than primary grade, if desired or required. Water classified as ASTM1193-96 purified, ASTM1193-96 ultrapure or higher can be used is desired or required.

Where desired or required, the composition can also include between 5 and 2000 ppm of pharmaceutically acceptable Group I ions, pharmaceutically acceptable Group II ions and mixtures thereof. In certain embodiments, ions can be selected from the group consisting of calcium, magnesium, strontium and mixtures thereof. In certain embodiments, the concentration of inorganic ion can be between 5 and 900 ppm; between 5 and 800 ppm; between 5 and 700 ppm; between 5 and 600 ppm; between 5 and 500 ppm; between 5 and 400 ppm; between 5 and 300 ppm; 5 and 200 ppm; between 5 and 100 ppm; between 5 and 50 ppm; between 5 and 30 ppm; between 5 and 20 ppm; between 10 and 900 ppm; between 10 and 800 ppm; between 10 and 700 ppm; between 10 and 600 ppm; between 10 and 500 ppm; between 10 and 400 ppm; between 10 and 300 ppm; 10 and 200 ppm; between 10 and 100 ppm; between 10 and 50 ppm; between 10 and 30 ppm; between 100 and 900 ppm; between 100 and 800 ppm; between 100 and 700 ppm; between 100 and 600 ppm; between 100 and 500 ppm; between 100 and 400 ppm; between 100 and 300 ppm; between 200 and 900 ppm; between 200 and 800 ppm; between 200 and 700 ppm; between 200 and 600 ppm; between 200 and 500 ppm; between 200 and 400 ppm; between 200 and 300 ppm; between 300 and 900 ppm;

between 300 and 800 ppm; between 300 and 700 ppm; between 300 and 600 ppm; between 300 and 500 ppm; between 300 and 400 ppm. In certain embodiments, the calcium ions can be present as $Ca^{2+}$, $CaSO_4^{-1}$, and mixtures thereof.

It is contemplated that the acid compound or compounds that is admixed can be produced by any suitable means that results in a material that has limited to no harmful interaction when introduced into contact with at least one region present in the respiratory tract of the patient.

The pharmaceutically acceptable fluid can also include at least one active pharmaceutical ingredient present in suitable therapeutic concentrations. Suitable active pharmaceutical ingredients can be those that have activity that is localized to the region of the respiratory tract to which it is brought into contact. It is also within the purview of this disclosure that suitable active pharmaceutical ingredients can be those which have effect on the larger respiratory system and/or the general systemic effect on the patient. In certain embodiments, the active pharmaceutical ingredient(s) employed can be those which can be administered through the pulmonary system by inhalation or the like. In certain embodiments, it is contemplated that the active pharmaceutical ingredient can be administered as part of a usage or treatment regimen using administration methods other than other than inhalation such as orally or intravenously.

As used herein "Active Pharmaceutical Ingredient" can also include "derivatives" of an Active Pharmaceutical Ingredient, such as, pharmaceutically acceptable salts, solvates, complexes, polymorphs, prodrugs, stereoisomers, geometric isomers, tautomers, active metabolites and the like. Preferably, derivatives include prodrugs and active metabolites. Furthermore, the various "Active Pharmaceutical Ingredients and derivatives thereof" are described in various literature articles, patents and published patent applications and are well known to a person skilled in the art.

In certain embodiments, the at least one active pharmaceutical ingredient can include one or more suitable compounds from classes such as antimicrobials such as antivirals or antibiotics, adrenergic $\beta_2$ receptor agonists, steroids, non-steroidal anti-inflammatory compounds, muscarinic antagonists, and the like. In certain embodiments, the pharmaceutically acceptable fluid as disclosed herein can include antiviral compounds with specific or general efficacy against coronaviruses, influenza, and the like to address and treat specific pathogenic infections. Nonlimiting examples of antiviral active pharmaceutical ingredient(s) include one or more compounds selected from the group consisting of amantadine, Lopinavir, linebacker and equivir, Arbidol, a nanoviricide, remdesivir, favipiravir, oseltamivir ribavirin, molnupiravir, and derivatives and prodrugs thereof as well as combinations of the foregoing. In certain situations, the antiviral active pharmaceutical ingredient(s) can be present in the form that will permit administration via inhalation or other suitable administration into direct or immediate contact with at least a portion of the respiratory tract of the patient. Without being bound to any theory it is believed that the materials such as molnupiravir may be present as a prodrug that could be converted by esterases in the lung to its active metabolite. Combination with the pharmaceutically acceptable fluid administered into contact with the at least one portion of the respiratory tract of the patient in need thereof thereby enhancing bioavailability and/or eliminating one or more side effects of the material administered by other methods.

It is also contemplated that, where desired or required, the antiviral drug can be administered as part of a use or treatment regimen. Orally or intravenously administered antivirals such as neuraminidase inhibitors, Cap-dependent endonuclease inhibitors and the like can be included in a use or treatment regimen.

In certain embodiments, the pharmaceutically acceptable fluid as disclosed herein can include antiviral compounds with specific or general efficacy against coronaviruses, influenza, and the like to address and treat specific pathogenic infections. Non-limiting examples of such antiviral compounds include remdesivir, molnupiravir and the like. The present disclosure contemplates the use of such materials in suitable combination with the pharmaceutically acceptable fluid disclosed herein used prophylactically either upon exposure or routinely, as with at-risk patient populations such as those with chronic illnesses or recognized co-morbidities. The present disclosure also contemplates administration or use of such materials in suitable combination with the pharmaceutically acceptable fluid disclosed hereinafter confirmed diagnosis to symptomatic or asymptomatic individuals. Without being bound to any theory, it is believed that the treatment with or use of the combination as disclosed can provide an effective therapy regimen to address respiratory illnesses including but not limited to SARS-CoV-2, influenza, and the like.

In certain embodiments, the pharmaceutically acceptable fluid can include at least one adrenergic $\beta_2$ receptor agonist active pharmaceutical ingredient. Suitable adrenergic $\beta_2$ receptor agonists can be those that can be administered by inhalation or other methods of introduction into contact with at least one region of the respiratory tract of the patient. Without being bound to any theory, it is believed that the adrenergic $\beta_2$ receptor agonists that are employed can act to cause localized smooth muscle dilation that can result in dilation of bronchial passages. Non-limiting examples of adrenergic $\beta_2$ receptor agonist that can be employed in the pharmaceutically acceptable fluid as disclosed herein can include those selected from the group consisting of bitolterol, fenoterol, isoprenaline, levosalbutamol, orciprenaline, pirbuterol, procaterol, ritodrine, salbutamol, terbutaline, albuterol, arformoterol, bambuterol, clenbuterol, formoterol, salmeterol, abediterol, carmoterol, indacaterol, olodaterol, vilanterol, isoxsuprine, mabuterol, zilpaterol, and mixtures thereof.

It is contemplated that, in certain situations, the adrenergic $\beta_2$ receptor agonist can be administered in a composition in combination with the pharmaceutically acceptable fluid. It is also contemplated the adrenergic $\beta_2$ receptor agonist can be co-administered with the with the pharmaceutically acceptable fluid disclosed herein.

In certain embodiments, the pharmaceutically acceptable fluid can include at least one steroid medication selected from the group consisting of compounds such as beclomethasone, budesonide, ciclesonide, flunisolide, fluticasone, mometasone, and combinations thereof. It is contemplated that, in certain situations, the steroid can be administered in a composition in combination with the pharmaceutically acceptable fluid. It is also contemplated the steroid can be co-administered with the pharmaceutically acceptable fluid disclosed herein.

In certain embodiments, the pharmaceutically acceptable fluid can include at least one inhalable non-steroidal medication such as those selected from the group consisting of compounds such as metabisulphite, adenosine, L-aspirin, indomethacin and combinations thereof.

It is contemplated that, in certain situations, the non-steroidal medication can be administered in a composition in combination with the pharmaceutically acceptable fluid. It is also contemplated the non-steroidal medication can be co-administered with the pharmaceutically acceptable fluid disclosed herein.

In certain embodiments, muscarinic antagonists can be one or more compounds selected from the group consisting of atropine, scopolamine, glycopyrrolate, and ipratropium bromide and the like.

The method as disclosed herein can be employed as a stand-alone treatment regimen or can be employed in combination with other therapy regimens suitable to address and treat the specific respiratory infection. The method can also be used alone or in combination with one or more procedures that can be employed prophylactically to reduce or minimize the risk or symptoms for individuals subsequent to exposure but prior to the onset of symptoms. It is also contemplated that the method as disclosed herein can be employed as a stand-alone treatment regimen for use for individuals at risk for complications or sub-optimal outcomes from respiratory infections. Non-limiting examples of such individuals include those with compromised immune systems, compromised pulmonary function, cardiac challenges, as well as co-morbidities such as age, body weight (obesity) and the like.

The method as disclosed herein can also include the step of administering a composition comprising hypochlorous acid, hydrogen peroxide and mixtures thereof into contact with the at least one region the respiratory tract of the patient. The administration of hypochlorous acid, hydrogen peroxide and mixtures thereof can occur prior to or contemporaneous with the step in which at least one dose of a pharmaceutically acceptable fluid is brought into contact with the at least one region of the respiratory tract of the patient. In certain embodiments, it is contemplated that the composition comprising hypochlorous acid, hydrogen peroxide and mixtures thereof can be co-administered with the pharmaceutically acceptable fluid material as disclosed herein. Where desired or required, the composition comprising hypochlorous acid, hydrogen peroxide and mixtures thereof as dispersed can be configured or sized to contact the same region of the respiratory tract as the pharmaceutically acceptable fluid material or different region.

Where desired or required pharmaceutically acceptable fluid material can be nebulized, aerosolized, or made into a particulate to facilitate administration. Administration of fluid material can be accomplished by direct application as swabbing, spraying, rinsing, emersion, and the like. It is also contemplated that aerosolized or nebulized material can be administered by inhalation if desired or required.

Where the various materials that constitute the pharmaceutically acceptable fluid are aerosolized or nebulized, the pharmaceutically acceptable fluid material(s) can be processed into droplets having a size suitable for inhalation uptake. Non-limiting examples of suitable droplet size include droplets having sizes between 0.1 and 20 μm; between 0.1 and 18 μm; between 0.1 and 17 μm; between 0.1 and 16 μm; between 0.1 and 15 μm; between 0.1 and 14 μm; between 0.1 and 13 μm; between 0.1 and 12 μm; between 0.1 and 12 μm; between 0.1 and 11 μm; between 0.1 and 10 μm; between 0.1 and 9 μm; between 0.1 and 8 μm; between 0.1 and 7 μm; between 0.1 and 6 μm; between 0.1 and 5 μm; between 0.1 and 4 μm; between 0.1 and 3 μm; between 0.1 and 2 μm; between 0.1 and 1 μm; between 0.1 and 0.5 μm; 0.5 and 20 μm; between 0.5 and 18 μm; between 0.5 and 17 μm; between 0.5 and 16 μm; between 0.5 and 15 μm; between 0.5 and 14 μm; between 0.5 and 13 μm; between 0.5 and 12 μm; between 0.5 and 12 μm; between 0.5 and 11 μm; between 0.5 and 10 μm; between 0.5 and 9 μm; between 0.5 and 8 μm; between 0.5 and 7 μm; between 0.5 and 6 μm; between 0.5 and 5 μm; between 0.5 and 4 μm; between 0.5 and 3 μm; between 0.5 and 2 μm; between 0.5 and 1 μm; between 1 and 20 μm; between 1 and 18 μm; between 1 and 17 μm; between 1 and 16 μm; between 1 and 15 μm; between 1 and 14 μm; between 1 and 13 μm; between 1 and 12 μm; between 1 and 11 μm; between 1 and 10 μm; between 1 and 9 μm; between 1 and 8 μm; between 1 and 7 μm; between 1 and 6 μm; between 1 and 5 μm; between 1 and 4 μm; between 1 and 3 μm; between 1 and 2 μm; between 2 and 20 μm; between 2 and 18 μm; between 2 and 17 μm; between 2 and 16 μm; between 2 and 15 μm; between 2 and 14 μm; between 2 and 13 μm; between 2 and 12 μm; between 2 and 11 μm; between 2 and 10 μm; between 2 and 9 μm; between 2 and 8 μm; between 2 and 7 μm; between 2 and 6 μm; between 2 and 5 μm; between 2 and 4 μm; between 2 and 3 μm.

Where desired or required, the acid compound(s) employed can be selected based on the pharmacodynamics and/or pharmacokinetics of the acid compound(s). In certain embodiments of the low pH antimicrobial inhalant making up the pharmaceutically acceptable fluid material can include a dilute sulfuric acid formulation due to its desirable pharmacodynamics and pharmacokinetics. It is believed that the sulfuric acid material will undergo a redox reaction to generate protons (H+) to be absorbed in the mucosa while the sulfate anions will be non-specifically biodistributed into the surrounding tissue for immediate clearance. Unless exposure is excessive, the anion distribution to the body's electrolyte pool is believed to be negligible. Without being bound to any theory, it is believed that the effects of sulfuric acid are the result of the H+ ion (local deposition of H+, pH change) rather than an effect of the sulfate ion. Sulfuric acid per se is not expected to be absorbed or distributed throughout the body. The acid will rapidly dissociate, and the anion will enter the body electrolyte pool, and will not play a specific toxicological role. (See OECD SIDS Sulfuric Acid, 2001, UNEP Publications, p102). As result little or no systemic effect is expected from dilute inhaled sulfuric acid aerosol, and the only effect will be local to the surfaces of the respiratory system.

The local effect of the released protons can inactivate viruses and other pathogens targeting the mucosal lining of the pulmonary epithelium and endothelium. Dilute sulfuric acid at the therapeutic concentration (~1.7 pH) provides efficacy at inactivating and/or reducing concentration of human coronavirus within 1 minute based on in vitro suspension tests.

At the proposed exposure concentrations, the resulting proton levels have not demonstrated toxicity on human cells and pulmonary vasculature, likely due to a highly buffered tissue microenvironment that is robust to this short-term change in interspatial pH. This has been shown by acute tissue toxicity and cytotoxicity studies performed within Good Laboratory Practice (GLP) guidelines.

Inhaled inorganic acids such as sulfuric acid at the concentrations contemplated in the present disclosure rapidly dissociate within the proximal pulmonary architecture, absorbing the sulfate ions into the bloodstream. Dahl studied the absorption of $^{35}S$ radiolabeled sulfuric acid in rats, guinea pigs, and dogs, revealing that rat and guinea pig animal models have very similar PK/PD parameters with 170 and 230 second $^{35}S$ half-lives. The half-life of the $^{35}S$ radiolabeled sulfuric acid in the dog studies varied significantly depending on the specific respiratory system administration site. Deep-lung sulfuric acid administration demonstrated a 2-3 minute half-life similar to the rats and guinea pigs. The half-life was significantly longer for administration to higher regions within the bronchi and sinus cavities. (see Dahl, Clearance of Sulfuric Acid-Introduced $^{35}S$ from the Respiratory Tracks of Rats, Guinea Pigs and Dogs Following Inhalation or Instillation, Fundamental and Applied Toxicology 3:293-297 (1983)).

The therapeutic inhalant demonstrates anti-viral therapeutic potential in the peripheral lung tissues with a half-life of ~2-3 minutes until absorption. Although sulfuric acid neutralization was not directly measured within the respiratory system, previous in vitro studies predict virus, bacteria, and fungi replication inhibition within 1 minute.

Also disclosed herein is a kit for use in the treatment or prevention of a respiratory illness that includes at least one container for administering the pharmaceutically acceptable fluid into the respiratory tract of a patient in need thereof that is connectable to a respiratory delivery device having at least one chamber. The at least one chamber contains at least one dose of a pharmaceutically acceptable fluid as disclosed herein. The pharmaceutically acceptable fluid includes a liquid carrier and at least one acid compound, wherein the pharmaceutically acceptable fluid has a pH less than 3.0 and a container for administering the pharmaceutically acceptable fluid into the respiratory tract of a patient in need thereof.

The kit can also include means for administering the pharmaceutically acceptable fluid to at least a portion of the respiratory tract of the patient in need thereof. Non-limiting examples of suitable means for administering the pharmaceutically acceptable fluid to at least a portion of the respiratory tract of the patient in need thereof can include devices like inhalers, metered dose inhalers, nebulizers such as PARI nebulizers and the like. The administering means can include at least one mechanism that delivers the fluid in a vaporized, atomized, or nebulized state. "Nebulizer" as the term is used herein is a drug delivery device used to administer medication in a form that can be inhaled into the lungs using oxygen, compressed air, ultrasonic power, or the like to break up solutions into small aerosol droplets. Non-limiting examples of nebulizers that can be used to dispense the pharmaceutically acceptable fluid as disclosed herein can be a jet nebulizer, a soft mist inhaler, an ultrasonic nebulizer, or the like. PARI nebulizers are commercially available PARI Respiratory Equipment, Inc., Midlothian Va.

The kit can also include a suitable mask or oral insert to direct material into the oral and/or nasal cavity of the patient.

Also disclosed is a respiratory inhalant device that includes a reservoir having at least one interior chamber and a dispenser in fluid communication with the reservoir. The container includes pharmaceutically acceptable fluid as disclosed herein contained in the at least one interior chamber.

The respiratory inhalant device also includes a dispenser in fluid communication with the reservoir that is configured to dispense a measured portion of the pharmaceutically acceptable fluid from the reservoir into inhalable contact with at least one portion of a respiratory tract of a patient having a respiratory illness. The pharmaceutically acceptable fluid dispensed in a droplet size between 0.5 and 5.0 microns mean mass diameter. In certain embodiments, the dispenser can include suitable tubing and an outlet member. The outlet member can be configured as a mask that can be removably fitted to the patient or a pipe-like member that can be removably inserted into the mouth of the patient, in certain embodiments. Other delivery members may include nasal cannulae, or the like.

The respiratory illness can be at least one of a viral pathogen, a bacterial pathogen, a fungal pathogen such as a viral pathogen such as one of coronavirus, an influenza virus, a parainfluenza virus, respiratory syncytial virus, a rhinovirus. In certain embodiments, the viral pathogen can be a beta coronavirus selected from the group consisting of SARS-CoV, SARS-CoV-2, MERS-CoV, and mixtures thereof.

In order to further illustrate the present disclosure, the following examples are presented. The Examples are for illustration purposes and are not to be considered limitative of the present disclosure.

EXAMPLE 1

Safety Evaluation of Various Components for Use in an Antimicrobial Inhalation Therapeutic An antimicrobial respiratory inhalant composed of the pharmaceutically acceptable fluid according to the present disclosure was prepared by admixing a pharmaceutically acceptable grade of sulfuric acid with water to provide pH in the various values indicated in the examples as follow.

1. Purpose: A low pH antimicrobial respiratory inhalant using a pharmaceutically acceptable fluid formulation of dilute sulfuric acid and a small concentration of calcium was tested for safety in vivo using acute toxicity studies in animals and later in humans. In vitro cytotoxicity tests were also performed.

In vitro suspension tests using dilute sulfuric acid against human coronavirus were used to assist in determining the minimum concentration required to demonstrate in vitro efficacy at 1 minute. A 1-minute suspension test is considered to be the most representative in vitro test to simulate in vivo efficacy based on previously discussed pharmacokinetics. A 1 log or 90% efficacy target has been chosen with consideration of patient recovery, while minimizing the effective concentration and potential patient risk. In one contemplated method of administration as described in the present disclosure, the material is administered to the patient in need thereof by inhalation by nebulizer. It is contemplated that patients using an inhalation method such as nebulizer administration would be inhaling the therapeutic material comprising a pharmaceutically acceptable fluid as disclosed herein continuously for several minutes in a specific concentration either continuously or in a series of discrete dose intervals with potentially multiple times per day potentially over multiple days. As a result, any reduction in pathogen load in vitro may be compounded in vivo to achieve higher efficacy over the treatment period. Thus, it is believed that an in vitro efficacy such as that demonstrated in the tests discussed herein that is lower than 1 log may provide an acceptable efficacy in vivo when administered as outlined herein.

It was shown that at 1.61 pH sulfuric acid demonstrates 0.75 log (82.11%) in vitro suspension efficacy in 1 minute. A slightly weaker and more conservative 1.72 pH (0.12%) sulfuric acid formulation was chosen to reduce viral load and assist in patient recovery from COVID-19.

2. In Vivo Acute Toxicity: GLP (Good Laboratory Practices) reported Acute Toxicity studies were performed with a formulation of sulfuric acid solution 50 times more concentrated than an inhalation therapeutic prepared according to the present disclosure. These studies included acute inhalation toxicity, acute oral toxicity, acute dermal toxicity, skin sensitivity, eye sensitivity and Local Lymph Node Assay (LLNA).

All six acute toxicity studies demonstrated little to no toxicity with a 50X concentration version of the therapeutic inhalation formulation. Since this is a respiratory inhalant, the acute inhalation toxicity study is particularly important. This study with 5 male and 5 female rats, demonstrated irregular breathing after dosing, but all 10 rats recovered. The results are summarized in Table 1.

TABLE 1

Dosing Comparison of Acute Inhalant Toxicity and Clinical Trial

| | Formulation for Acute Inhalation Toxicity | Formulation for Phase 1 Clinical Trial |
|---|---|---|
| Sulfuric Acid concentration | 5.2% | 0.12% |
| pH | ~0.5 pH | 1.72 pH |
| Acid concentration comparison | 50X | 1X |
| Applicator | Nebulizer[1] | Nebulizer[2] |
| Mean Mass Aerodynamic Diameter | 2.19 um[1] | 3.1 um[2] |
| Gravimetric Concentration | 5.12 mg/L[1] | 22 mg/L[2] |
| Treatment Frequency | Single 4 hour dose[1] (240 minutes) | 4 mL (~9 minutes[2]) 3-4X daily, up to 7 days[3] (up to 252 minutes) |

[1]GLP Acute Toxicity Study

[2]PARI LC STAR nebulizer specification https://www.pari.com/us-en/products/nebulizers/lcr-star-reusable-nebulizer/(retrieved Oct. 15, 2021)

The 50X concentration formulation with 5.2% sulfuric acid demonstrated no acute inhalation toxicity, while a more diluted concentration of 0.12% demonstrated in vitro efficacy on human coronavirus indicated that such material would exhibit efficacy against respiratory infections caused by human coronaviruses including but not limited to beta coronaviruses such as SARS-CoV-2 which encouraged further research into use as a potential antimicrobial respiratory inhalant, and First-in-Human Clinical Trials 3. In Vitro Cytotoxicity: GLP Cytotoxic Assays on the L929 mouse cell line using 4 different concentrations were carried out in accordance with ISO 10993-5 and the results are summarized in the Table 2. All four concentrations including those at 250% of the therapeutic concentration showed no sign of biological reactivity Grade 0—No detectable zone around or under specimen.

TABLE 2

Cytotoxicity Study Results

| Sulfuric Acid % | Concentration Relative to Therapeutic | Test Results | Cytotoxicity Grade |
|---|---|---|---|
| 0.30% | 2.5X | No biological reactivity | Grade 0 |
| 0.24% | 2.0X | No biological reactivity | Grade 0 |
| 0.18% | 1.5X | No biological reactivity | Grade 0 |
| 0.12% | 1X | No biological reactivity | Grade 0 |

EXAMPLES 2-13

In order to assess the antimicrobial efficacy of various acid compounds and combinations, a variety of potential pharmaceutically acceptable fluid formulations within the scope of the present disclosure were evaluated to determine antimicrobial efficacy against common viral, bacterial, and fungal pathogens. These studies were all performed by an ISO 17025 Accredited and GLP Compliant Laboratory. These in vitro tests followed ASTM (American Society of Testing and Materials) standard suspension tests for antimicrobial efficacy. The tests were all performed with a 1-minute contact time based on the pharmacokinetics previously described.

Efficacy of Various Proposed Antimicrobial Inhalation Therapeutic vs. Antibiotic Resistant Microorganisms Purpose: The first set of in vitro efficacy tests were performed on antibiotic resistant *Staphylococcus aureus* and *Pseudomonas aeruginosa* bacteria. These two antibiotic resistant bacterial strains were initially selected since these pathogens represent two broad classes of bacteria. *S. aureus* is Gram-positive and *P. aeruginosa* is Gram-negative. Antibiotic resistant strains of each pathogen are considered some of the deadliest respiratory bacterial strains with limited therapeutic options.

Results: The results of these tests are shown in Table 3.

TABLE 3

Sulfuric Add Efficacy vs antibiotic resistant *Staphylococcus aureus* (MRSA) and *Pseudomonas aeruginosa*

| | Formulation | Pathogen | pH As Received | pH As Applied | Efficacy Log | Efficacy % |
|---|---|---|---|---|---|---|
| 2 | Sulfuric Acid | *S. aureus* | 1.8 | 1.9 | 0.005 | 1.18% |
| 3 | Sulfuric Acid | *S. aureus* | 3.0 | 3.1 | 0.09 | 18.24% |
| 4 | Sulfuric + Calcium | *S. aureus* | 1.8 | 1.9 | 0.03 | 6.47% |
| 5 | Sulfuric + Calcium | *S. aureus* | 3.0 | 3.1 | 0.05 | 10.59% |
| 6 | Sulfuric + Albuterol | *S. aureus* | 1.8 | 1.9 | 0.07 | 15.29% |
| 7 | Sulfuric + Albuterol | *S. aureus* | 3.0 | 3.1 | 0.14 | 27.06% |
| 8 | Sulfuric Acid | *P. aeruginosa* | 1.8 | 1.9 | 4.46 | 99.997% |
| 9 | Sulfuric Acid | *P. aeruginosa* | 3.0 | 3.1 | 0.05 | 11.07% |
| 10 | Sulfuric + Calcium | *P. aeruginosa* | 1.8 | 1.9 | 4.16 | 99.99% |
| 11 | Sulfuric + Calcium | *P. aeruginosa* | 3.0 | 3.1 | no reduction | no reduction |
| 12 | Sulfuric + Albuterol | *P. aeruginosa* | 1.8 | 1.9 | >4.46 | >99.997% |
| 13 | Sulfuric + Albuterol | *P. aeruginosa* | 3.0 | 3.1 | 0.006 | 1.38% |

Test conditions:

Tested In Accordance With ASTM E2315, 1 minute, no soiling, non-GLP, single-replicant Bacteria tested: *Staphylococcus aureus* ATCC (MRSA) 33591 and *Pseudomonas aeruginosa* ATCC BAA-2801

The as-received pH measurements were of the test materials as received by the test laboratory. The ASTM antimicrobial test procedures mix 9 parts test material with 1 part medium containing the pathogen. The as-applied pH is the pH after mixing, which is what is seen by the pathogen. After the test duration, 1 minute for these tests, the test material is neutralized, and the pathogens are counted and compared with the control.

Conclusions: None of the formulations, either at 1.9 or 3.1 pH demonstrated appreciable effect on *S. aureus*, vis à vis the 1 log reduction target adopted for these evaluations. All of the formulations at 1.9 pH were effective against antibiotic resistant *P. aeruginosa*, but none of the 3.1 pH formulations demonstrated the effectiveness at the defined target level.

In order to study the antimicrobial effect of known APIs when formulated with the composition as disclosed herein, samples of the test composition were formulated with albuterol, an established respiratory API at a standard therapeutic concentration of 0.0063M albuterol. The results are summarized in the Table 3 and indicated that established APIs do not significantly affect the antimicrobial efficacy of the composition.

EXAMPLE 14

Efficacy of Reformulated Albuterol Inhalation Therapeutic vs, Antibiotic Resistant Microorganisms Purpose: This comparative example discusses the potential of reformulating one of the world's most common respiratory inhalants, Albuterol sulfate, in order to provide new antimicrobial properties. Albuterol is typically formulated with sulfuric acid as an adduct to enhance stability and shelf-life of the active albuterol ingredient. Albuterol sulfate has been used for decades without harmful effects including regularly by asthmatics, a patient population that has higher sensitivity to respiratory irritants. The pH of albuterol is typically 3.5.

The composition was composed of sulfuric acid plus albuterol formulation at 3.1 pH that was tested closely matches a commercial albuterol sulfate formulation at the low end of the pH range with this well-established therapeutic.

Results: Albuterol sulfate as available and administered is not recognized to have any antimicrobial properties. Albuterol sulfate tests conducted confirm that albuterol sulfate at its lowest therapeutically approved pH of 3.1 demonstrated no efficacy against *S. aureus* or *P. aeruginosa* bacteria as determined by 1 log decrease in pathogen count at one minute.

The tests also demonstrate that by increasing the concentration of sulfuric acid in the albuterol sulfate therapeutic new antimicrobial efficacy is achieved against an antibiotic resistant strain of *Pseudomonas aeruginosa* as outlined in Examples 12 and 13.

Conclusions: Multidrug resistant *Pseudomonas aeruginosa* has one of the higher mortality rates of any respiratory bacterial infection, particularly in patients with chronic respiratory diseases such as cystic fibrosis and chronic obstructive pulmonary disease. These tests demonstrate that the widely used albuterol sulfate therapeutic, when reformulated with additional sulfuric acid can function as a potential therapeutic against this pathogen and may have particular utility for populations with pre-existing chronic respiratory diseases.

EXAMPLES 15-42

Efficacy of Various Acid Antimicrobial Inhalation Therapeutics vs *Streptococcus pneumoniae*

Purpose: *Streptococcus pneumoniae* is a leading cause of bacterial pneumonia, meningitis, and sepsis, and is estimated to have caused approximately 335,000 (240,000-460,000) deaths in children aged <5 years in 2015 globally. Due to the prevalence and mortality of *S. pneumoniae* a wide range of acid formulations were tested against this common pathogen to determine what variables may affect efficacy. The purpose of the tests performed was to determine what pH is required to achieve 1 log (90%) efficacy in 1 minute against *S. pneumoniae* using various acid formulations.

Results: The results of these tests are shown in Tables 4 and 5.

TABLE 4

Compounds Evaluated

| Ref. | Compound |
|---|---|
| A | Sulfuric acid |
| B | Hydrobromic acid |
| C | Isoascorbic acid |
| D | Trichloroacetic acid |
| E | Hydrochloric acid |
| F | Bensenesulfonic acid |
| G | Phosphoric acid |
| H | Polyphosphoric acid |
| I | Hydroxyacetic acid |
| J | Monochloroacetic acid |
| K | Trifluoroacetic acid |
| L | Aspartic acid |
| M | Glutamic acid |
| N | Albuterol |
| O | Ethanol |
| P | Salmeterol |
| Q | Ciclesonide |
| R | Vilanterol |
| S | Adenosine |
| T | Calcium |

TABLE 5

Efficacy of Various Acid Formulations vs *Streptococcus pneumoniae*

| Ex | Compound 1 | Compound 2 | Compound 3 | Distilled Water | pH as received | pH after dilution | Eff (Log) | Eff (Percent) |
|---|---|---|---|---|---|---|---|---|
| 15 | A (0.0647 g) | N (0.0798 g) | — | 52.424 g | 1.755 | 1.871 | 1.523 | 97.00% |
| 16 | A (0.0985 g) | O (1.0355 g) | P (0.0022 g) | 51.914 g | 1.562 | 1.678 | 4.38 | 99.99% |
| 17 | A (0.0719 g) | Q (0.0040 g) | — | 52.422 g | 1.783 | 1.899 | 0.98 | 89.58% |
| 18 | A (0.08597 g) | O (1.4320 g) | R (0.0050 g) | 58.148 g | 1.814 | 1.93 | 1.35 | 95.58% |
| 19 | C (3.23 g) | — | — | 105.00 g | 2.305 | 2.421 | no reduction | no reduction |
| 20 | A (0.0789 g) | — | — | 63.629 g | 1.795 | 1.911 | 1.11 | 92.25% |
| 21 | A (0.011g) | — | — | 89.594 g | 2.475 | 2.591 | no reduction | no reduction |

TABLE 5-continued

Efficacy of Various Acid Formulations vs *Streptococcus pneumoniae*

| Ex | Compound 1 | Compound 2 | Compound 3 | Distilled Water | pH as received | pH after dilution | Eff (Log) | Eff (Percent) |
|---|---|---|---|---|---|---|---|---|
| 22 | A (0.095 g) | S (0.168 g) | — | 52.11 g | 1.798 | 1.914 | 2.12 | 99.25% |
| 23 | A (0.1618 g) | — | — | 109.301 g | 1.92 | 2.036 | 0.019 | 4.24% |
| 24 | A (0.0635 g) | — | — | 109.45 g | 2.123 | 2.239 | no reduction | no reduction |
| 25 | B (0.191 g) | — | — | 152.127 g | 1.899 | 2.015 | no reduction | no reduction |
| 26 | B (0.101 g) | — | — | 156.85 g | 2.161 | 2.277 | 0.04 | 9.32% |
| 27 | E (0.090 g) | — | — | 155.645 g | 1.879 | 1.995 | no reduction | no reduction |
| 28 | E (0.0439 g) | — | — | 154.00 g | 2.178 | 2.294 | no reduction | no reduction |
| 29 | | C (3.100 g) | — | 102.58 g | 1.85 | 1.966 | no reduction | no reduction |
| 30 | D (0.287 g) | — | — | 122.901 g | 1.874 | 1.99 | 2.15 | 99.29% |
| 31 | E (0.0801 g) | — | — | 112.461 g | 1.759 | 1.875 | 0.715 | 80.70% |
| 32 | B (0.0862 g) | — | — | 106.321 g | 1.787 | 1.903 | 1.045 | 90.99% |
| 33 | E (0.136 g) | S (0.093 g) | — | 143.898 g | 1.802 | 1.918 | 0.658 | 78.03% |
| 34 | E (0.081 g) | C (13.306 g) | — | 116.092 g | 1.785 | 1.901 | 4.01* | 99.99%* |
| 35 | F (0.311 g) | — | — | 115.624 g | 1.85 | 1.966 | 1.36 | 95.61% |
| 36 | G (0.0641 g) | — | — | 121.120 g | 1.81 | 1.926 | 0.51* | 69.30%* |
| 37 | H (0.931 g) | — | — | 131.126 g | 1.79 | 1.906 | 0.95 | 88.77% |
| 38 | I (11.17 g) | — | — | 70.10 g | 1.82 | 1.936 | >4.36 | >99.996% |
| 39 | J (2.513 g) | — | — | 102.101 g | 1.80 | 1.916 | >5.36 | >99.9996% |
| 40 | K (0.354 g) | — | — | 169.414 g | 1.90 | 2.016 | >5.36 | >99.9996% |
| 41 | E (0.137 g) | L (0.379 g) | — | 120.193 g | 1.86 | 1.976 | 0.66 | 78.07% |
| 42 | E (0.422 g) | M (0.644 g) | — | 169.93 g | 1.86 | 1.976 | 0.62 | 76.14% |

Note:
all ingredients are shown normalized to 100% activity. All raw materials were USP grade.
Bacterial tested: *Streptococcus pneumoniae* ATCC 6303.
Tested in accordance with ASTM E2315, 1 minute, no soiling, non-GLP, single-replicant
*neutralization did not occur.

Conclusion: Adding respiratory APIs such as bronchodilators, steroids, and non-steroidal anti-inflammatories did not significantly change the efficacy. This suggests that new formulations of these established APIs may be prepared that offer new antimicrobial properties to patient populations that may be particularly susceptible to these pathogens.

Several inorganic acids were tested to determine effective pH to meet the 1 log efficacy target. A 1.91 pH value for sulfuric acid (example 20) was found to meet this target. Similarly, a 1.90 pH value for hydrobromic acid (example 32); a value of approximately 1.87 pH for hydrochloric acid (example 33) and an approximately 1.85 pH value for polyphosphoric acid (example 37) achieved this target.

The stronger organic acids including benzenesulfonic acid, trichloroacetic acid, hydroxyacetic acid, monochloroacetic acid and trifluoroacetic acid exhibit higher efficacy than the inorganic acids in the range of 1.9 pH (example 35 and examples 38-40).

The weaker organic acids, when used alone, generally cannot reach the required pH range of <2.0 pH required for efficacy. However, these weaker organic acids can be mixed with inorganic acids to meet the desired pH range of <2.0, and these mixed acid solutions of a weak organic and inorganic acid can demonstrate better efficacy than the inorganic acid alone at the same pH level.

Amino acids are weak organic acids that are pharmaceutically acceptable and can be formulated with stronger inorganic acids to provide improved efficacy. Two of the more acidic amino acids are aspartic acid and glutamic acid. Formulation of aspartic acid or glutamic acid and hydrochloric acid at 1.98 pH exhibit 0.62-0.66 log efficacy while hydrochloric at the same pH level exhibits no little efficacy (examples 41, 42 and 27). Adding aspartic acid or glutamic acid to inorganic acids such as sulfuric, hydrochloric and hydrobromic may offer better efficacy in a higher pH formulation with less deleterious effect.

COMPARATIVE EXAMPLE 1—Acetic Acid

Acetic acid inhalation has been proposed as a potential adjunctive therapy for non-severe COVID-19. (See L. Pianta, Acetic acid disinfection as a potential adjunctive therapy for non-severe COVID-19, European Archives of Oto-Rhino-Laryngology, May 2020). The results of efficacy and tolerability studies are discussed to determine if acetic acid could be used as an acidic antimicrobial inhalant therapeutic. Studies indicate that acetic acid has demonstrated efficacy as a disinfectant on hard surfaces against the SARS-CoV-2 virus with 4 log efficacy in 1 minute using a 4% concentration with a 2.68 pH. (see J. Yoshimoto, Virucidal effect of acetic acid and vinegar on SARS-CoV-2).

In the Pianta study, twenty-nine patients inhaled 0.35% acetic acid as an adjunct therapy with hydroxychloroquine. The inhalant was delivered by placing the patient's face over the steaming acid solution and covering the head and bowl with a cloth. The steam mist aerosol size and concentration were not controlled. A 0.35% acetic acid concentration was measured to have a pH of approximately 2.98. An acetic acid concentration of 0.35% at or above 3.0 pH and is unlikely to have any antimicrobial benefits.

An acetic acid inhalation tolerance study was performed with 5 men and 5 women healthy volunteers. Discomfort in the nose, burning, irritated or runny nose was noted at levels as low as at 10 ppm (0.001%) with 118-minute exposure. (see L. Ernstgard, Acute effects of exposure to vapors of acetic acid human, Toxicology Letters 165 (2006) 22-30).

Conclusions: The disinfectant efficacy study, the therapeutic inhalation study and the inhalation tolerance study all used different concentrations of acetic acid with different pH values as summarized in Table 6.

TABLE 6

Concentration and pH of Acetic Acid Studies

| Acetic Acid Study | Acetic Acid Concentration (%) | Acetic Acid Concentration (ppm) | pH |
|---|---|---|---|
| Disinfectant | 4% | 40,000 | 2.68 |
| Antimicrobial Inhalant | 0.35% | 350 | 2.98 |
| Inhalant Tolerability | 0.01% | 10 | 3.77 |

A 0.35% acetic acid concentration was measured to have a pH of approximately 2.98, and a 0.01% concentration was measured to have a pH of 3.77

High concentrations of acetic acid with a pH at 2.68 can be an effective disinfectant to inactivate the SARS-CoV-2 virus. At very low concentrations, with a pH of 3.77, acetic acid demonstrates patient irritability issues. At the 2.98 pH concentration acetic acid used in the antimicrobial therapeutic study it unlikely to have any antimicrobial benefit. Additionally, if acetic acid at this concentration is applied consistently with significant mist density (gravimetric concentration) it is expected to cause patient irritability.

In order to be an effective acidic antimicrobial formulation, the material must not cause patient tolerability issues at the therapeutic concentration. Acetic acid fails the patient tolerability criteria.

While many factors may affect patient tolerance, it is believed that various pharmaceutically acceptable acids with poor patient tolerance profiles, such as organic acids like acetic acid may be employed in combination with one or more acid or adjuvants with more acceptable profiles in or to provide a pharmaceutically acceptable fluid or composition that is more tolerable to the patient to whom it is administered.

EXAMPLES 43-54

Efficacy vs Common Bacterial and Fungal Respiratory Pathogens

Purpose: The purpose of this study was to determine how effective Sulfuric acid is against a range of common bacterial and fungal respiratory pathogens. Sulfuric acid has demonstrated efficacy vs Gram-negative *P. aeruginosa* and Gram-positive *S. pneumoniae* bacteria, but it is desirable to understand how effective it may be against other respiratory pathogens, and what concentration (pH) is required to achieve 1 log efficacy in 1 minute. Three other bacteria and three fungi were selected that represent a wide variety of respiratory pathogens.

Results: The results are summarized in Table 7.

TABLE 7

Efficacy of Sulfuric Acid Composition vs Common Bacterial and Fungal Respiratory Pathogens

| | Pathogen | pH As Received | pH As Applied | Efficacy Log | Efficacy % |
|---|---|---|---|---|---|
| 43 | *K. pneumoniae* | 1.871 | 1.987 | 5.22 | >99.99% |
| 44 | *K. pneumoniae* | 2.163 | 2.279 | 0.88 | 86.97% |
| 45 | *H. influenzae* | 1.871 | 1.987 | >6.94 | >99.9999% |
| 46 | *H. influenzae* | 2.163 | 2.279 | >6.94 | >99.9999% |

TABLE 7-continued

Efficacy of Sulfuric Acid Composition vs Common Bacterial and Fungal Respiratory Pathogens

| | Pathogen | pH As Received | pH As Applied | Efficacy Log | Efficacy % |
|---|---|---|---|---|---|
| 47 | *M. terrae* | 1.871 | 1.987 | 0.12 | 24.56% |
| 48 | *M. terrae* | 2.163 | 2.279 | 0.02 | 5.56% |
| 49 | *A. fumigatus* | 1.871 | 1.987 | 1.66 | 97.83% |
| 50 | *A. fumigatus* | 2.163 | 2.279 | 1.7 | 98.00% |
| 51 | *R. microsporus* | 1.871 | 1.987 | 1.73 | 98.13% |
| 52 | *R. microsporus* | 2.163 | 2.279 | 1.73 | 98.13% |
| 53 | *C. neoformans* | 1.871 | 1.987 | 0.03 | 6.43% |
| 54 | *C. neoformans* | 2.163 | 2.279 | 0.04 | 9.36% |

Test conditions:
Tested In Accordance With ASTM E2315, 1 minute, no soiling, non-GLP, single-replicant
Bacteria tested: *Klebsiella pneumoniae* ATCC 4532, *Haemophilus influenza* ATCC 8149, *Mycobacterium terrae* ATCC 15755
Fungi tested: *Aspergillus fumigatus* ATCC 36607, *Rhizopus microspores* ATCC 52807, *Cryptococcous neoformans* ATCC 66031

Conclusions: It is noted that 1.99 pH sulfuric acid is highly effective against both *Klebsiella pneumoniae* and *Haemophilus* influenza. In previous studies it was demonstrated that 1.9 pH sulfuric acid was effective on antibiotic resistant *P. aeruginosa*. These three bacteria are sometimes considered to be some of the most common Gram-negative bacterial respiratory pathogens. This supports a conclusion that formulations of sulfuric acid at 1.9 pH and below may be effective against all Gram-negative respiratory bacteria, both antibiotic sensitive and antibiotic resistant.

The sulfuric acid formulation outlined above demonstrates limited efficacy (0.12 log/25%) on *Mycobacterium terrae*, used as a surrogate for *Mycobacterium tuberculosis*.

The 1.9 pH sulfuric acid formulation was effective on *Aspergillus fumigatus* and *Rhizopus* microspores demonstrating efficacy against some forms of fungi. It is also noted that *R. microsporus* is a spore producing fungi, and these results appear to support conclusions of efficacy at killing fungi spores as well as active forms of the fungi.

EXAMPLE 55

Efficacy of Sulfuric Acid and Aspartic Acid Combination Inhalation Therapeutic vs *Mycobacterium terrae*

Purpose: *Mycobacterium terrae* is recognized as a surrogate for *Mycobacterium Tuberculosis*, which is one of the world's most deadly pathogens. In 2015 *M. tuberculosis* killed 1.4 million people, making it the greatest single infectious agent cause of death in the world (prior to COVID-19). Over 10 million new cases of tuberculosis are diagnosed annually with growing percentage having multi-drug resistant infections. (see Forum of International Respiratory Societies. The Global Impact of Respiratory Disease—Second Edition. Sheffield, European Respiratory Society, 2017)

Results: The 1.99 pH sulfuric acid formulation demonstrated modest efficacy (0.12 log 24.56%) on *M. terrae*. Even at modest in vitro efficacy this formulation may have therapeutic efficacy due to the compounding efficacy from continuous administration. This may be beneficial for tuberculosis patients, and particularly those suffering with antibiotic resistant strains.

A more concentrated sulfuric formulation with a pH of 1.6 with or without Aspartic acid added demonstrates a 1 log efficacy against *M. terrae* in 1 minute.

Conclusions: Acidic antimicrobial inhalation therapeutics are a promising new therapeutic approach to the global issue of tuberculosis. A sulfuric acid formulation with a pH of 1.6 with or without aspartic acid appears promising and may be used alone or as an adjunct therapeutic with established antibiotics. The sulfuric acid formulation is anticipated to be equally effective on antibiotic sensitive and antibiotic resistant strains for *M. tuberculosis*.

Unlike the antibiotic therapeutics that are known to have significant side effects in some tuberculosis patents, acidic antimicrobial inhalant therapeutic as disclosed herein may have minimal or no side effects and be easy to administer to large patient populations.

EXAMPLE 56-63

Efficacy of Inorganic Acid Antimicrobial Inhalant Therapeutics vs Human Coronavirus Purpose: COVID-19 is a global pandemic caused by the SARS-CoV-2 coronavirus. The purpose of these studies was to determine the efficacy of several inorganic acids against the human coronavirus and ascertain the pH required to achieve 1 log efficacy in 1 minute.

SARS-CoV-2 is a beta coronavirus. An alpha coronavirus was used in these studies since this was the closest virus available at the test laboratory. The alpha coronavirus is considered to be representative for efficacy on SARS-CoV-2 for purposes of this investigation.

Results: The test results of these studies are shown in Table 8.

TABLE 8

Efficacy of Inorganic Acids vs Human Coronavirus

| | Formulation | pH As Received | pH As Applied | Efficacy Log | Efficacy % |
|---|---|---|---|---|---|
| 56 | Sulfuric | 1.771 | 1.967 | 0.5 | 68.38% |
| 57 | Sulfuric | 1.865 | 2.061 | no reduction | no reduction |
| 58 | Sulfuric | 1.996 | 2.192 | 0.25 | 43.77% |
| 59 | Sulfuric | 2.048 | 2.244 | 0.25 | 43.77% |
| 60 | Hydrochloric | 1.799 | 1.995 | no reduction | no reduction |
| 61 | Hydrochloric | 2.038 | 2.234 | 0.25 | 43.77% |
| 62 | Hydrobromic | 1.752 | 1.948 | 0.5 | 68.38% |
| 63 | Hydrobromic | 2.036 | 2.232 | 0.25 | 43.77% |

Test conditions:
Tested In Accordance With ASTM E1052, 1 minute, no soiling, non-GLP, single-replicant
Virus tested: Human Coronavirus, 229E strain, ATCC VR-740

The viral medium used was EMEM (Eagle's Minimum Essential Medium) which has a larger effect at increasing the pH between As Received and As Applied than that demonstrated with the bacteria medium. Due to the larger increase in pH, none of the acids achieved the 1 log efficacy goal.

The EMEM includes live MRC-5 cells which have significant buffer capacity. Lower pH sulfuric acid formulations employed to repeat the efficacy test vs human coronavirus demonstrate 1 log efficacy.

Conclusions: It was determined that additional viral tests were needed with lower as-received pH.

EXAMPLE 64-69

Efficacy of Sulfuric Acid Antimicrobial Inhalant Therapeutics vs Selected Respiratory Viruses Purpose: Antimicrobial inhalant concentrations of sulfuric acid were tested for efficacy against Human Coronavirus, Alpha Influenzavirus and Rhinovirus to determine how effective these materials may be as a therapeutic inhalant.

Results: The results of these studies are shown in Table 9.

TABLE 9

Efficacy of Sulfuric Acid vs Selected Respiratory Viruses

| | Pathogen | pH As Received | pH As Applied | Efficacy Log | Efficacy % |
|---|---|---|---|---|---|
| 64 | Human Coronarvirus | 1.273 | 1.616 | 0.75 | 82.11% |
| 65 | Human Coronarvirus | 1.542 | 1.765 | 0.25 | 43.77% |
| 66 | Influenza A virus | 1.411 | 1.657 | >5log | >99.999% |
| 67 | Influenza A virus | 1.607 | 1.897 | >5log | >99.999% |
| 68 | Rhinovirus | 1.258 | 1.469 | >4log | >99.99% |
| 69 | Rhinovirus | 1.458 | 1.6 | >4log | >99.99% |

Test conditions:
Tested In Accordance With ASTM E1052, 1 minute, no soiling, non-GLP, single-replicant
Virus tested: Human Coronavirus, 229E strain, ATCC VR-740; Influenza A (H1N1) A/PR/8/34 Strain; Rhinovirus 37

Conclusions: A sulfuric acid formulation with 1.62 pH demonstrated 0.75 log or 82.11% efficacy in 1 minute almost meeting the 1 log efficacy goal against the human coronavirus pathogen and a similar efficacy is predicted for the SARS-CoV-2 coronavirus. As discussed previously due to the continuous inhalation of the nebulizer treatment, therapeutic efficacy over the treatment period is compounded from the in vitro efficacy results.

A lower 1.72 pH sulfuric acid formulation was selected for First-in-Human Clinical Trials to further reduce patient risk.

A 1.90 sulfuric acid formulation demonstrated >5 log efficacy against an alpha influenza virus. Influenza A is responsible for seasonal flus and the efficacy against this virus may indicate efficacy against this serious pathogen.

A 1.60 pH sulfuric acid formulation demonstrated >4 log efficacy against a rhinovirus. The rhinovirus is the most common viral infectious agent in humans and is the predominant cause of the common cold. Efficacy against this virus may indicate efficacy against this common pathogen.

Coronaviruses, influenza viruses and rhinoviruses are all encapsulated respiratory viruses. These tests demonstrate efficacy against all of the common encapsulated respiratory viruses tested using a sulfuric acid formulation of 1.6 pH and below. Based on these results it may be assumed that this formulation would be effective on all encapsulated respiratory viruses in an inhalation setting

EXAMPLE 70

Simplified Therapeutic Process and Preparation for Inhalation Therapy for Individuals Presenting with COVID-19

1. Therapeutic Package Material: Various 5 vol % solutions of a pharmaceutically acceptable grade of sulfuric acid alone, hydrochloric acid alone or a 50-50 mixture of sulfuric acid and hydrochloric acid, respectively, are prepared and are diluted with deionized water at a ratio of four parts water to 1part material and are packaged in 2 oz/60 ml glass bottles with droppers.

2. Therapeutic Administration: An aliquot of 4 ml of the Therapeutic Packaged Material is introduced into a PARI nebulizer to produce a particle size of 2.9 μm Mean Mass Aerodynamic Diameter (MMAD) that can be administered to each respective subject via inhalation though as suitable nebulizer mask. The 4 mL dose is anticipated to produce aerosolized sulfuric acid for about 10 minutes, which is one treatment.

3. Human Clinical Study: 20 individuals with confirmed cases of COVID 19 as confirmed by PCR testing and presenting with various respiratory symptoms up to an including Acute Respiratory Distress each receive 4 ml doses, every 3 to 4 hours, 4 times daily (10-minute treatment each) for 7 days via nebulizer with daily observation for 14 days after the beginning of treatment and then follow-up observations after 3 weeks, 4 weeks and 3 months. The administrations are well-tolerated results in lessening of physical symptoms after 24 hours in most patients with a portion of the patients testing negative for COVID after 72 hours.

For each composition, an additional 100 individuals with confirmed cases of COVID 19 as confirmed by PCR testing and presenting with various respiratory symptoms up to and including Acute Respiratory Distress each receive 4 ml doses, every 3 to 4 hours, 4 times daily (10-minute treatment each) for 7 days via nebulizer. To assess the efficacy of material as disclosed herein, subjects are randomized to either Arm A who will receive the therapeutic composition of (67 individuals) while 33 condition and age-matched subjects receive a placebo of normal saline solution. Treatment commences immediately upon confirmation of COVID 19 with follow-up visits for 14 days post-treatment; at Weeks 3 and 4 after the completion of treatment; and at Month 3 post-treatment.

Certain individuals receiving one of the therapeutic compositions experience reduction of symptoms commencing subsequent to receipt of the first or second dose as measured by blood oxygenation levels and/or reduction in chest congestion. This result is not mirrored in the control group. A significant number of individuals receiving one of the therapeutic compositions tested negative for COVID-19 after 3 to 7 days of treatment as measured by PCR.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A system for treating a respiratory illness caused by at least one of MERS, SARS CoV-1, SARS CoV-2 comprising:

a medication delivery device comprising a nebulizer or a metered dose inhaler, the medication delivery device having a medication chamber and a medication outlet member in fluid communication with the medication chamber; and a pharmaceutically acceptable therapeutic inhalation fluid composition present in the medication chamber and deliverable through the medication outlet, the pharmaceutically acceptable therapeutic inhalation fluid composition consisting of:

a fluid carrier, wherein the fluid carrier is water; and a pharmaceutically acceptable acidic component, the pharmaceutically acceptable acidic component consisting of at least one organic acid and at least one inorganic acid, the at least one organic acid selected from the group consisting of trichloroacetic acid, benzenesulfonic acid, propionic acid, formic acid, gluconic acid, lactic acid, ascorbic acid, isoascorbic acid, aspartic acid, glutamic acid, glutaric acid, hydroxyacetic acid and mixtures thereof, and the at least one inorganic acid selected from the group consisting of sulfuric acid, hydrochloric acid, hydrobromic acid, phosphoric acid, polyphosphoric acid, hypochlorous acid, and mixtures thereof, and optionally, an ionic component selected from the group of pharmaceutically acceptable Group I ions, pharmaceutically acceptable Group II ions, and mixtures thereof, wherein the pharmaceutically acceptable acidic component is present in the carrier in an amount sufficient, upon inhalation, for treating an infection in a patient caused by at least one of MERS, SARS CoV-1, or SARS CoV-2 wherein the pharmaceutically acceptable acidic component is present in an amount sufficient to produce a pH less than 2.0.

2. The system for treating the respiratory illness of claim 1 wherein the pharmaceutically acceptable inhalation fluid composition has a pH below 1.8.

3. The system of claim 2 wherein the pharmaceutically acceptable acid consists of sulfuric acid and an organic acid selected from the group consisting of trichloroacetic acid, benzenesulfonic acid, propionic acid, formic acid, gluconic acid, lactic acid, ascorbic acid, isoascorbic acid, aspartic acid, glutamic acid, glutaric acid, hydroxyacetic acid and mixtures thereof.

4. The system of claim 1 wherein the at least one organic acid is one of aspartic acid, isoascorbic acid, or hydroxyacetic acid, and the inorganic acid is one of sulfuric acid, hydrochloric acid or a mixture of sulfuric acid and hydrochloric acid.

5. The system of claim 4 wherein the pharmaceutically acceptable therapeutic inhalation fluid has a pH less than 1.8.

6. The system of claim 1 wherein the ionic component of the pharmaceutically acceptable inhalation fluid composition is calcium.

7. A system for treating a respiratory illness involving at least one of MERS, SARS CoV-1, SARS CoV-2, the system comprising:

a medication delivery device configured as a nebulizer, the medication delivery device having a medication chamber and a medication outlet member in fluid communication with the medication chamber; and a pharmaceutically acceptable therapeutic inhalation fluid composition contained in the medication chamber in the nebulizer, the pharmaceutically acceptable inhalation fluid composition consisting of:

an aqueous fluid carrier; and a pharmaceutically acceptable acidic component, the pharmaceutically acceptable acidic component consisting of at least one organic acid and at least one inorganic acid, wherein the organic acid is selected from the group consisting of trichloroacetic acid, benzenesulfonic acid, propionic acid, formic acid, gluconic acid, lactic acid, ascorbic acid, isoascorbic acid, aspartic acid, glutamic acid, glutaric acid, and mixtures thereof and the inorganic acid is selected from the group consisting of sulfuric acid, hydrochloric acid, hydrobromic acid, phosphoric acid, polyphosphoric acid, hypochlorous acid, and mixtures thereof, wherein the pharmaceutically acceptable acidic component is present in the carrier in an amount sufficient, upon inhalation, for treatment of a respiratory infection in a patient caused by at least one of MERS, SARS CoV-1, or SARS CoV-2 wherein the pharmaceutically acceptable acidic component is present in an amount sufficient to produce a pH less than 2.5.

8. The system of claim 7 wherein the pharmaceutically acceptable inhalation fluid composition has a pH below 1.8.

9. The system of claim 8, wherein the aqueous fluid carrier of the pharmaceutically acceptable inhalation fluid composition is water.

10. A system for treating a respiratory illness caused by one of MERS, SARS CoV-1, SARS CoV-2, the system comprising:

a medication delivery device comprising a nebulizer, the medication delivery device having a medication chamber and a medication outlet member in fluid communication with the medication chamber; and a pharmaceutically acceptable therapeutic inhalation fluid composition contained in the medication chamber and deliverable through the medication outlet member, the pharmaceutically acceptable therapeutic inhalation fluid consisting of:

an aqueous fluid carrier; and a pharmaceutically acceptable acidic component, the pharmaceutically acceptable acidic component consisting of at least one organic acid and at least one inorganic acid, wherein the at least one organic acid is selected from the group consisting of trichloroacetic acid, benzenesulfonic acid, propionic acid, formic acid, gluconic acid, lactic acid, ascorbic acid, isoascorbic acid, aspartic acid, glutamic acid, glutaric acid, and mixtures thereof, and the at least one inorganic acid is selected from the group consisting of sulfuric acid, hydrochloric acid, hydrobromic acid, hypochlorous acid, and mixtures thereof, wherein the pharmaceutically acceptable acidic component is present in the fluid carrier in an amount sufficient, upon inhalation, for treating an infection in a patient caused by at least one of MERS, SARS CoV-1, or SARS CoV-2 and wherein the pharmaceutically acceptable acidic component is present in an amount sufficient to produce a pH less than 2.0.

11. The system of claim 10 wherein the pharmaceutically acceptable inhalation fluid composition has a pH below 1.8.

12. The system of claim 11 wherein the aqueous fluid carrier of the pharmaceutically acceptable inhalation fluid composition is water.

13. The system of claim 10 wherein the organic acid of the pharmaceutically acceptable inhalation fluid composition is selected from ascorbic acid, isoascorbic acid and mixtures thereof, and the inorganic acid is selected from the group consisting of sulfuric acid, hydrochloric acid, hydrobromic acid, phosphoric acid, polyphosphoric acid, hypochlorous acid, and mixtures thereof.

14. The system of claim 10 wherein the medication delivery device is configured to produce a pharmaceutically acceptable inhalation fluid having a particle size between 0.1 and 5.0 microns mean mass aerodynamic diameter when it exits the medication outlet member.

15. The system of claim 14 wherein the medication delivery device is configured to produce a pharmaceutically acceptable inhalation fluid composition that can be introduced into contact with at least one of the following: throat, pharynx, larynx, epiglottis, sinuses, trachea, bronchi, or alveoli.

* * * * *